United States Patent [19]

Moriuchi et al.

[11] Patent Number: 4,906,233
[45] Date of Patent: Mar. 6, 1990

[54] METHOD OF SECURING A CATHETER BODY TO A HUMAN SKIN SURFACE

[75] Inventors: Yousuke Moriuchi; Toshinobu Ishida; Tadashi Kousai, all of Fujinomiya, Japan

[73] Assignee: Terumo Kabushiki Kaisha, Tokyo, Japan

[21] Appl. No.: 232,799

[22] Filed: Aug. 16, 1988

Related U.S. Application Data

[63] Continuation-in-part of Ser. No. 54,313, May 26, 1987, abandoned.

[30] Foreign Application Priority Data

May 29, 1986 [JP] Japan ............................ 61-124337

[51] Int. Cl.4 .......................................... A61M 25/02
[52] U.S. Cl. ........................... 604/174; 128/DIG. 26; 128/784
[58] Field of Search ............... 604/174–180, 604/283; 128/DIG. 26, 784–786

[56] References Cited

U.S. PATENT DOCUMENTS

| | | | |
|---|---|---|---|
| 3,537,452 | 11/1970 | Wilks | 604/162 |
| 3,730,187 | 5/1973 | Reynolds | 604/178 |
| 3,834,380 | 9/1974 | Boyd | 604/180 |
| 4,435,174 | 3/1984 | Rechmond et al. | 604/174 |
| 4,480,639 | 11/1984 | Peterson et al. | 604/174 |
| 4,516,584 | 5/1985 | Garcia | 128/785 |
| 4,553,961 | 11/1985 | Pohndorf et al. | 604/174 X |
| 4,632,670 | 12/1986 | Mueller, Jr. | 604/174 |
| 4,645,492 | 2/1987 | Weeks | 604/174 |
| 4,650,473 | 3/1987 | Bartholomew et al. | 604/174 |
| 4,683,895 | 8/1987 | Pohndorf | 604/174 X |

FOREIGN PATENT DOCUMENTS 0093512 11/1983 European Pat. Off. .

Primary Examiner—Dalton L. Truluck
Attorney, Agent, or Firm—Frishauf, Holtz, Goodman & Woodward

[57] ABSTRACT

A method of firmly securing a catheter body to a surface portion of human skin, without causing the catheter body to be bent or reducing the diameter of the inner passage of the catheter body. This method employs a catheter-securing member which comprises a cylindrical body for allowing the catheter body to be slidably inserted therein, and a slit is provided along the axial direction of the cylindrical body. In this method a ligature is first pierced through a surface portion of human skin and tied over the surface of human skin, leaving a pair of free end portions extending out of the skin, and then the cylindrical body is secured with the free end portions of the ligature by winding the ligature around the cylindrical body and fastening them.

6 Claims, 2 Drawing Sheets

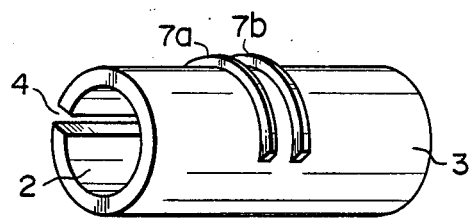
F I G. 4
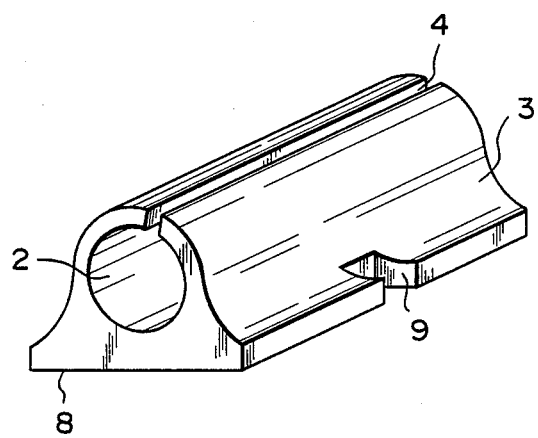
F I G. 5

METHOD OF SECURING A CATHETER BODY TO A HUMAN SKIN SURFACE

CROSS-REFERENCE TO THE RELATED APPLICATION

This application is a continuation-in-part of application Ser. No. 054,313 filed on May 26, 1987, and now abandoned.

BACKGROUND OF THE INVENTION (a) Field of the Invention

The present invention relates to a method of securing a catheter body to a human skin for a long period of time.

(b) Description of the Prior Art

An intravenous catheter (to be referred to hereinafter as an IVH catheter) is widely used for high calorie fluid therapy. Other various catheters have been also used for long-term indwelling in human body (e.g., in a vein).

A distal portion of the IVH catheter or the like is inserted into a vein by using, for example, the hollow needle method or the cut-down method. The part of the catheter outside of the body needs to be secured in place, to avoid being accidently moved. When such a catheter is indwelled in the body, a sepsis may occur as a complication. It is said that the cause of the sepsis is bacteria entering the body from the outside of the catheter, and that the rate of occurrence of the sepsis increases when the catheter is not secured firmly to the body.

Conventional methods of securing the catheter are: securing the part of the catheter outside of the body by using surgical tape; forming a subcutaneous tunnel and inserting the catheter with a Dacron cuff thereinto; and securing in place by suturing, with a ligature, the portion of the catheter outside of the body in the skin. In the method using the surgical tape, the catheter can still be easily moved, and therefore this method is not reliable. In the method of forming the subcutaneous tunnel, the catheter can be secured firmly in place. However, this operation is too complicated to be widely employed. Since a catheter of this type, e.g., an IVH catheter is normally indwelled for one or two weeks, the method of suturing the catheter in the skin by means of a ligature is widely employed as an easy-to-perform and reliable method.

However, using this method, the catheter may be broken at the portion tied by the ligature, or the cavity of the catheter may become so narrowed that a transfusion liquid cannot be supplied into the catheter at a predetermined flow rate.

SUMMARY OF THE INVENTION

It is an object of the present invention to solve the conventional problems described above and to provide a method of securing a catheter body to a human skin in such a manner that the catheter body will not be broken at a portion tied by a ligature, and a cavity thereof not be narrowed, and hence a transfusion liquid can be reliably supplied into the catheter, at a predetermined flow rate, and also provide a catheter-securing member which allows the catheter to be easily and firmly secured to the skin.

More specifically, according to the present invention, a securing member is provided which allows the catheter to be firmly secured to the surface of the skin, and which is constituted by a cylindrical body having a hollow portion into which the catheter body is slidably inserted in its axial direction, the cylindrical body having a slit formed to extend along the axial direction of the cylindrical body, and the slit reaching the hollow portion. Furthermore, according to the present invention, there is provided a method of securing a catheter body to a surface portion of human skin, which comprises;

preparing a cylindrical body having a hollow portion into which said catheter body is slidably inserted in an axial direction of said cylindrical body, said cylindrical body having a slit formed to extend along the axial direction of said cylindrical body, and said slit reaching said hollow portion;

piercing a middle portion of a ligature through a surface portion of human skin and tieing the middle portion of the ligature over the surface portion of human skin, extending a pair of free end portions of said ligature out of the skin for fastening said cylindrical body;

securing said cylindrical body with said pair of free end portions of the ligature by winding said ligature around said cylindrical body and fastening said ligature, thereby securing the catheter body to a surface portion of human skin.

BRIEF DESCRIPTION OF THE DRAWINGS

FIGS. 4 and 5 are respectively perspective views showing other modifications of the catheter-securing member according to the present invention.

DETAILED DESCRIPTION OF THE PREFERRED EMBODIMENTS

The present invention will now be described, with reference to an embodiment shown in the accompanying drawings.

Figure 1:
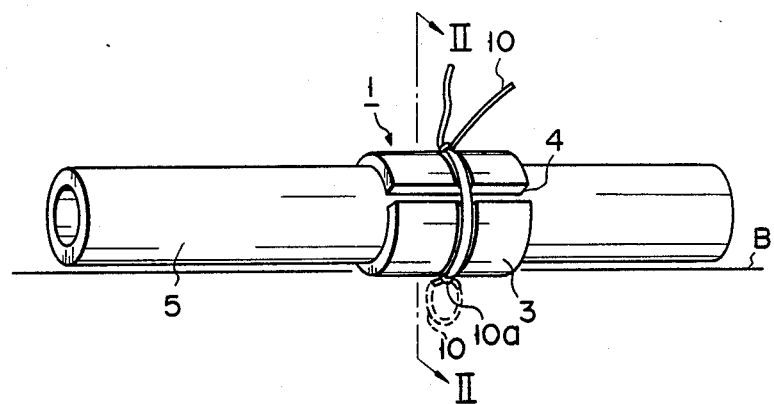
FIG. 1 is a perspective view of a state wherein the catheter-securing member mounted on the catheter body is secured on a surface portion of human skin.

FIG. 1 is a perspective view of catheter-securing member 1 mounted on a catheter body 5 and secured to human skin B with a strip of ligature 10 according to the present invention. The catheter-securing member 1 comprises a cylindrical body 3 having hollow portion 2 into which a catheter body is slidably inserted in an axial direction thereof. Slit 4, reaching hollow portion 2, is formed from one end to the other end of catheter-securing member 1, along the axial direction thereof.

Figure 3:
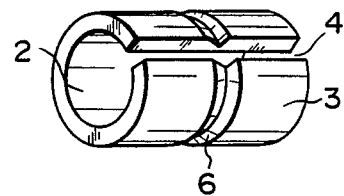
FIG. 3 is a perspective view of a catheter-securing member according to the present invention.

The catheter-securing member 1 is also provided as shown in FIG. 3 with an annular groove 6, which is circumferentially formed to traverse an axial direction of cylindrical body 3, and is preferably formed in a direction perpendicular to the axial direction thereof.

Annular groove 6 need not necessarily be formed around the center circumferential surface of member 1, but may be formed on a portion thereof, so long as it can prevent the ligature from being moved. Annular groove 6 may be formed in a V-shaped, a V-shape, or any other shape.

Catheter-securing member 1 is preferably made of a flexible synthetic resin material, and more preferably made of a material having a high elasticity. Examples of such a material are a soft vinyl chloride resin, rubber (e.g., silicone rubber and latex rubber), polypropylene, polyethylene, and polyurethane. The length of member 1 is not limited, but is preferably 3 to 30 mm, and more preferably 5 to 15 mm, to ensure secure tying of a ligature on member 1, and ease of handling.

Slit 4 may extend along the axial direction of the catheter body, or it may extend parallel, at an oblique angle, or spirally in relative to the axial direction of the catheter body, and preferably be arranged parallel to the axis of the catheter body. Slit 4 may be formed by simply cutting member 1. Member 1 is fitted on the catheter body, and this cut portion serves as slit 4. Slit 4 may have a predetermined width. If member 1 is fitted on the catheter body and the width of slit 4 is not more than 1/5 or preferably not more than 1/10 the overall circumferential length of member 1, the cavity of the catheter body will not be narrowed upon tying by the ligature.

The inner diameter of hollow portion 2 is slightly larger than the outer diameter of the catheter body, so that the catheter body can be moved therewithin. The difference in diameter between them may be determined such that when the catheter-securing member is tied with the ligature, to be fixed to the skin, it is brought into tight contact with and is firmly secured to the catheter body. The inner diameter of hollow portion 2 may alternatively be equal to or slightly smaller than the outer diameter of the catheter body. In this case, the catheter body can be rendered movable by enlarging slit 4.

Catheter body 5 is a tube whose distal and proximal ends are open, and is made of a soft resin. Examples of the soft resin which can be used are silicone rubber, a soft vinyl chloride resin, and a polyurethane elastomer.

In the conventional IVH catheter, a catheter body having an inner diameter of 0.5 to 1.7 mm and an outer diameter of 0.9 to 2.1 mm is used.

A catheter is fixed to the skin by using catheter-securing member 1 tied with a ligature as follows. In the first step, a single or a plurality of catheter-securing members 1 are indwelled, as is shown in FIG. 1, by inserting a predetermined portion of catheter body 5 into hollow portion 2. The position of catheter body 5 is shifted and adjusted within hollow portion 2, so as to determine the portion thereof to be tied with the ligature.

Then, ligature 10 is pierced into skin A, followed by temporarily fastening ligature 10 on skin A. Further, the ligature on skin A is wound about the catheter-securing member such that the ligature extends within annular groove 6 of the catheter-securing member. Under this condition, the free end portions of the ligature are tied to each other so as to fix catheter-securing member 1 and, thus, to fix catheter 5 to skin A via catheter-securing member 1.

FIG. 4, which illustrates a modification of catheter-securing member 1, shows that at least two ribs, 7a and 7b, may be circumferentially formed in place of annular groove 6, to extend along a portion of the outer surface of member 1, such that a groove is formed between the ribs.

FIG. 5, which illustrates another modification of catheter-securing member 1, shows that flat portion 8 is preferably formed at a portion of the outer surface of member 1, such that it extends along the axial direction thereof. A contact area of member 1 to the skin of human body is increased by forming flat portion 8, thereby allowing member 1 to be easily and firmly secured to the skin.

In the case of the modification shown in FIG. 5, in place of annular groove 6, a pair of notches 9 for preventing the ligature from being moved are formed at portions of both the edges of flat portion 8.

The same reference numerals in FIGS. 4 and 5 denote the same parts as in FIG. 3, and a description thereof will be omitted.

When a catheter-securing member according to the present invention is used for securing a catheter, for example in the case of an IVH catheter, a distal end of catheter body 5 is inserted into a vein, by means of the hollow needle method, and member 1 is shifted to a position where it can be secured to a portion of skin. The catheter is then secured in place, by means of ligature tied at a portion of member 1. Then, a high-calorie transfusion liquid is allowed to flow from a proximal end of catheter 5.

The catheter-securing member according to the present invention serves as a member for securing the catheter body to the skin. Since the catheter-securing member has an insertion portion for the catheter body, and can be moved along the axial direction thereof, the catheter body can be easily and firmly secured to any desired portion of the skin without being bent at a ligature portion or the cavity thereof being narrowed.

The catheter-securing member according to the present invention is not limited to the IVH catheter-securing member, but can be applied to any catheter which is indwelled in a body for a relatively long period of time.

Next, examples and a comparative example according to the present invention will be described.

EXAMPLE 1

A catheter composed of a soft vinyl chloride resin was constructed, having an outer diameter of 1.5 mm, an inner diameter of 0.8 mm, and having open distal and proximal ends. A catheter-securing member was made of a soft vinyl chloride resin was constructed in the form of a cylindrical tube having an inner diameter of 1.4 mm, an outer diameter of 3.0 mm, and a length of 6.0 mm, and having a slit in its axial direction. A catheter body was inserted into the catheter-securing member, so as to form the catheter according to the present invention. It should be noted that the above catheter-securing member could be easily moved in its axial direction.

Figure 2:
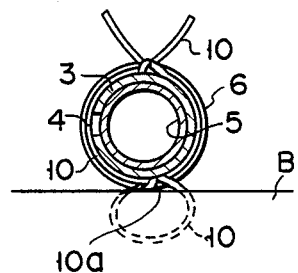
FIG. 2 is a sectional view as taken along the line II—II of FIG. 1.

The above-described catheter was tied as shown in FIGS. 1 and 2 to a rubber plate having a thickness of 6 mm, by using a No. 3 ligature at a portion of the catheter-securing member.

As a result, the catheter body could be easily and firmly secured to the rubber plate by means of the securing member. Furthermore, the catheter body was not bent and a cavity thereof was not narrowed upon fastening of the ligature around the catheter, nor did the catheter break off when it was pulled hard.

EXAMPLE 2

In this example, a catheter was arranged in the same manner as described in Example 1, except that an annular groove (a V-shaped groove having a depth of 0.5 mm) was circumferentially formed in a direction perpendicular to the axis of the catheter-securing member.

As was the case in Example 1, the catheter-securing member could be easily moved along the longitudinal axis of the catheter body.

The catheter was tied to a rubber plate having a thickness of 6 mm, by using the No. 3 ligature in the same manner as in Example 1, such that the ligature was fitted into the annular groove of the catheter-securing member.

As a result, the catheter body could be easily and firmly secured to the rubber plate, by the fixing member. Furthermore, the catheter body was not bent and the cavity thereof was not narrowed upon fastening of the ligature around the catheter, nor did the catheter break off when it was pulled hard. The ligature was not shifted when only the fixing member was pulled.

EXAMPLE 3

A catheter made of a soft vinyl chloride resin was constructed, having an inner diameter of 1.4 mm, a length of 6.0 mm, and an outer diameter of 3.0 mm at a thin wall portion. A flat portion having a length of 6.0 mm in the axial direction of the catheter-securing member and a length of 4.0 mm in a direction perpendicular to the axial direction thereof was formed on the securing member. A number of 0.8 mm deep notches were formed midway along the flat portion, at positions symmetrical about the axis of the securing member.

A catheter body as shown in Example 1 was used in this example. As was the case in Example 1, the catheter-securing member could be easily moved along the longitudinal axis of the catheter body.

The catheter was tied to the rubber plate having a thickness of 6 mm, by using the No. 3 ligature in the same manner as in Example 1, such that the ligature was fitted into the annular groove of the catheter-securing member. As a result, the catheter body could be easily and firmly secured to the rubber plate, by means of the securing member. Furthermore, the catheter body was not bent and the cavity thereof was not narrowed upon fastening of the ligature around the catheter. The catheter did not break off when it was pulled hard, nor did the ligature shift when only the catheter-securing member was pulled. It should be noted that in this example, the catheter-securing member was secured to the rubber plate more firmly than in the above examples.

COMPARATIVE EXAMPLE

In this example, a catheter made of a soft vinyl chloride resin was constructed, having an outer diameter of 1.5 mm and an inner diameter of 0.8 mm, and having open distal and proximal ends. The catheter was tied to the rubber plate having a thickness of 6 mm, by using the No. 3 ligature in the same manner as in Examples 1 to 3.

As a result, the cavity of the catheter was narrowed and the catheter body was bent at the ligature portion when it was sutured somewhat tightly. In addition, the catheter broke at the ligature portion when it was pulled hard.

What is claimed is:

1. A method of securing a catheter body to a surface portion of human skin, which comprises:
    preparing a cylindrical body to have (a) a hollow portion into which said catheter body is slidably inserted in an axial direction of said cylindrical body, and (b) a slit formed to extend from one end to the other end and along the axial direction of said cylindrical body, and said slit reaching said hollow portion;
    piercing a middle portion of a ligature through a surface portion of human skin, tying the middle portion of the ligature over the surface portion of human skin, and extending a pair of free end portions of said ligature out of the skin for fastening said cylindrical body; and
    securing said cylindrical body with said pair of free end portions of the ligature by winding said ligature around said cylindrical body and fastening said ligature to tighten the catheter body, thereby securing the cylindrical body as well as the catheter body to a surface portion of human skin.

2. A method according to claim 1, wherein a flat surface is formed on a portion of an outer surface of said catheter-securing member in the axial direction thereof.

3. A method according to claim 1, wherein said catheter-securing member is made of a flexible material.

4. A method according to claim 3, wherein an inner diameter of said hollow portion is slightly smaller than an outer diameter of said catheter body.

5. A method according to claim 1, wherein a groove for fitting said ligature therein is formed on at least a portion of an outer surface of said cylindrical body, so as to extend in a direction traversing an axial direction of said cylindrical body.

6. A method according to claim 1, wherein not less than two projections for fitting said ligature therein are formed on at least a portion of an outer surface of said cylindrical body, so as to extend in a direction traversing the axial direction of said cylindrical body.

* * * * *

UNITED STATES PATENT AND TRADEMARK OFFICE
CERTIFICATE OF CORRECTION

PATENT NO. : 4,906,233

DATED : March 6, 1990

INVENTOR(S) : Yousuke MORIUCHI et al

It is certified that error appears in the above-identified patent and that said Letters Patent is hereby corrected as shown below:

Column 2, line 63, change "V-shaped" to --V-shape--.

Column 2, line 63, change "V-shape" to --U-shape--.

Signed and Sealed this

Twenty-second Day of September, 1992

Attest:

DOUGLAS B. COMER

*Attesting Officer*     *Acting Commissioner of Patents and Trademarks*